US006290672B1

(12) United States Patent
Abae

(10) Patent No.: US 6,290,672 B1
(45) Date of Patent: *Sep. 18, 2001

(54) EXPLORATORY TUBULAR SONOGENIC CATHETER

(76) Inventor: Mick Abae, 1271 NW. 100th Way, Plantation, FL (US) 33322

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/902,657

(22) Filed: Jul. 30, 1997

(51) Int. Cl.$^7$ .................................................. A61M 29/00
(52) U.S. Cl. .................. 604/101.04; 604/48; 604/96.01; 604/97.02
(58) Field of Search ................................ 604/55, 96, 101, 604/102, 104, 96.01, 515, 97.02, 101.01, 101.03, 101.04, 101.05, 102.02, 514, 48

(56) References Cited

U.S. PATENT DOCUMENTS

| 2,113,246 | 4/1938 | Wappler . |
|---|---|---|
| 3,882,852 | 5/1975 | Sinnreich . |
| 3,948,259 | 4/1976 | Bolduc et al. . |
| 4,763,669 | 8/1988 | Jaeger . |
| 4,848,336 | 7/1989 | Fox et al. . |
| 4,863,716 | 9/1989 | Quay et al. . |
| 4,880,015 | 11/1989 | Nierman . |
| 4,911,163 * | 3/1990 | Fina . |
| 5,041,108 | 8/1991 | Fox et al. . |
| 5,104,377 | 4/1992 | Levine . |
| 5,180,367 * | 1/1993 | Kontos et al. . |
| 5,188,595 | 2/1993 | Jacobi . |
| 5,237,985 | 8/1993 | Hodgson et al. . |
| 5,289,831 * | 3/1994 | Bosley . |
| 5,300,023 | 4/1994 | Lowery et al. . |
| 5,327,891 | 7/1994 | Rammler . |
| 5,342,306 * | 8/1994 | Don Michael . |
| 5,419,763 * | 5/1995 | Hildebrand . |
| 5,423,742 * | 6/1995 | Theron . |
| 5,458,573 * | 10/1995 | Summers . |
| 5,458,583 * | 10/1995 | McNeely et al. . |
| 5,462,529 * | 10/1995 | Simpson et al. . |
| 5,464,409 | 11/1995 | Mohajer . |
| 5,496,271 * | 3/1996 | Burton et al. . |
| 5,571,115 | 11/1996 | Nicholas . |
| 5,624,399 * | 4/1997 | Ackerman . |
| 5,662,609 * | 9/1997 | Slepian . |
| 5,665,063 * | 9/1997 | Roth et al. . |

* cited by examiner

Primary Examiner—Richard K. Seidel
Assistant Examiner—Cris Rodriguez
(74) Attorney, Agent, or Firm—Malin, Haley and Dimaggio, P.A.

(57) ABSTRACT

An improved catheter for delivery of a saline solution to a fallopian tube to be examined by ultrasonic energy and for filling the uterus with a saline solution simultaneously in a sealed position. The device uses first and second expandable balloon sealing elements, one for the fallopian tube opening, the other for the cervix opening to completely seal the fallopian tube and the uterus. The distance between the balloons is adjustable, and a catheterization tip is insertable through a lumen into the fallopian tube. Liquid is provided to the balloons through separate lumens that include cutoff valves for holding the liquid in the balloons. The method employed involves inserting the distal end of the device into the uterus opening while positioning the balloon within the cervical opening and positioning a second balloon in the fallopian tube. The method then includes expanding both balloons so that the cervix and then the fallopian tube are sealed tightly. The catheterization wire can include an echogenic tip for improved ultrasonic testing.

5 Claims, 3 Drawing Sheets

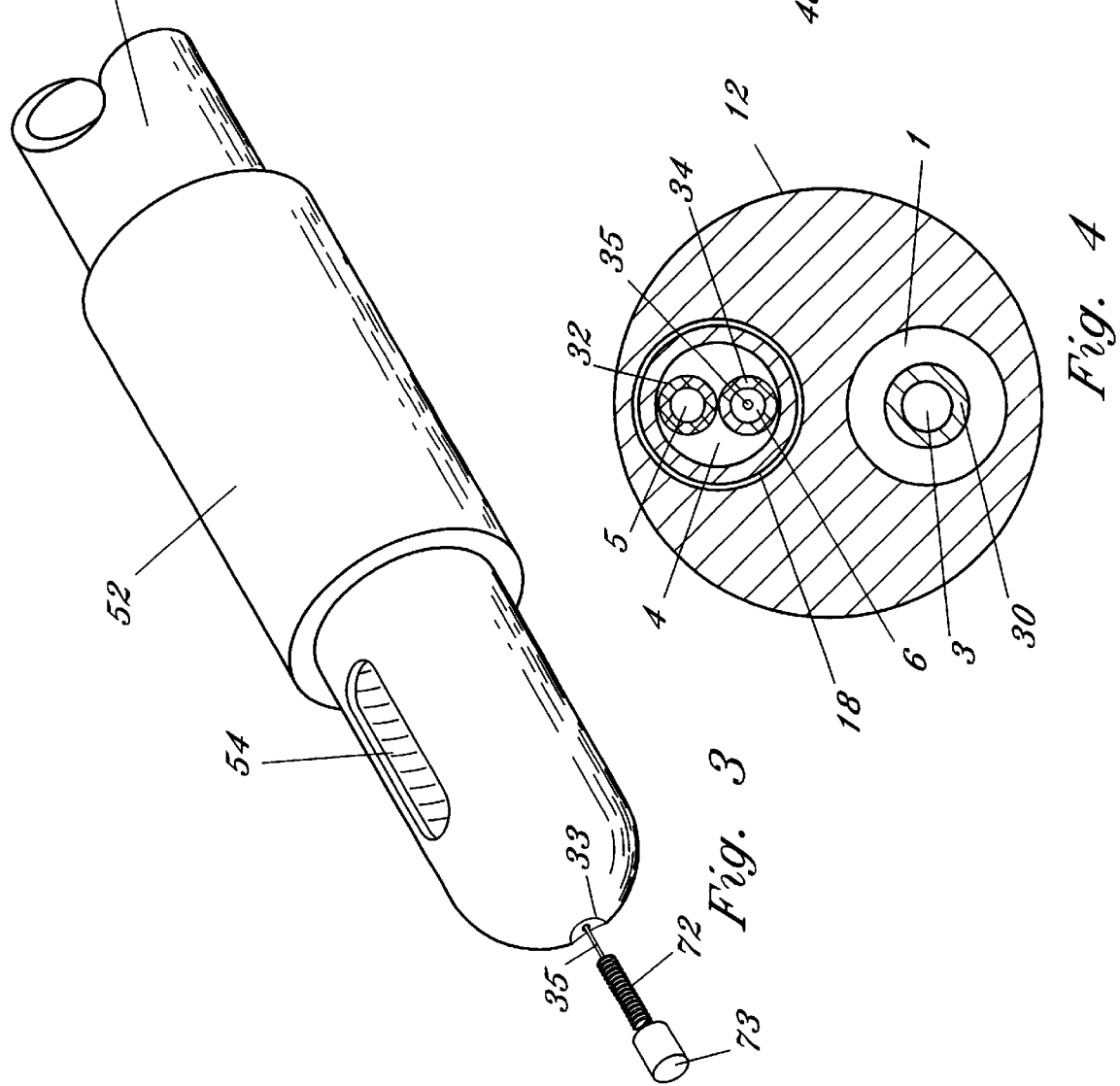

EXPLORATORY TUBULAR SONOGENIC CATHETER

BACKGROUND OF THE INVENTION

1. Field of the Invention

This invention relates to an improved catheter for dispensing fluid within a fallopian tube and uterus in conjunction with expandable balloons for sealing the entrance to the fallopian tube and uterus to allow the injection of a saline fluid for improving uterine and fallopian tube ultrasonic examination and to provide for corrective procedures such as catheterization of blockages.

2. Description of the Background Art

Using present day state of the art equipment, surgeons can perform medical procedures to open a closed or blocked fallopian tube. Sonograms and ultrasonics are employed to locate the entrance to the fallopian tube and the blockage in the fallopian tube, in conjunction with a saline fluid that is used to fill the uterus to aid in the ultrasonic locating process. The primary objective is to guide or aid, through the use of ultrasonics, the surgeon in locating obstructions in the fallopian tube. The use of ultrasonics is a desired method, but requires skill on the part of the surgeon to ultimately locate blockages within the fallopian tube. Saline fluid in the fallopian tube and the uterus is essential for proper ultrasonic examination results. Instruments may be utilized for catheterization of blockages in a fallopian tube once the obstruction is located.

The use of balloon catheters which allow for inflation of a balloon around the outside of the catheter and injection of a fluid or liquid while simultaneously placing the balloon against the walls of an opening has been used for filling the uterus with a saline solution.

Devices are known in the prior art for introducing fluids into the uterine cavity and, ultimately, into the fallopian tubes. U.S. Pat. No. 3,948,259, issued Apr. 6, 1976 to Bolduc et al., describes a dispensing instrument for placing a material in the uterine cavity and moving the material from the uterine cavity through the canals of the fallopian tubes of a female. U.S. Pat. No. 5,188,595, issued Feb. 23, 1993 to Jocobi, discloses a method for enhanced retention of a balloon catheter in a body cavity which uses a pair of inflatable balloons which have a device for forming a suction between them to act to positively retain the catheter in position in a body cavity. U.S. Pat. No. 5,104,377, issued Apr. 14, 1992 to Levine, describes a uterine access device with an automatic cervical adjustment. The device includes expandable distal and proximate members to secure a shaft to the uterus by adjusting to the length of the cervical canal.

None of the prior art references describe a catheter to assist in inspection of the fallopian tubes using ultrasonics through the introduction of liquids into the fallopian tubes, as described in the present invention. The present invention may also be used for catheterization of blockages found in the fallopian tubes.

SUMMARY OF THE INVENTION

The present invention provides an improved catheter that permits diagnostic and therapeutic examination of the uterus and fallopian tubes using ultrasonics and can provide delivery and retention of a predetermined necessary liquid, such as saline, into the fallopian tube and the uterus for proper ultrasonic examinations.

Infertility in women is often the result of fallopian tube blockage. Blockage in the fallopian tube prevents the ova from reaching the uterus. It is therefore necessary for a physician or surgeon to determine whether or not there is any blockage occurring in the fallopian tube. One method of determining blockage is through the use of ultrasonics or ultrasound in the form of sonograms, which can provide imaging on a visual display that shows various physiological conditions present in the uterus and in the fallopian areas. In order to get a good sonogram or ultrasonic picture, it is essential that the areas in question contain the proper density of liquid, such as a saline solution, for best results.

The catheter in accordance with the present invention is comprised of a plurality of lumens joined together as a single unit having first and second expandable balloons adjustable between strategically determined locations relative to the proximal and distal ends of the lumens. Each expandable balloon is connected to a separate lumen that provides for liquid under pressure through a syringe piston disposed at the proximal end of the device.

Disposed adjacent each expandable balloon is a liquid orifice which is the termination of a particular lumen that provides for the proper fluid distribution from a piston or other fluid dispensing device that transmits fluid through the lumen for expulsion at the particular lumen orifice.

The present invention may also include a separate lumen having a probe with a distal end tip made of an echogenic material for improved visual display guidance using the sonogram. The echogenic tip will be more visible on the sonic display relative to the catheter probe end and the body tissue. The catheter may also provide for tissue catheterization with the echogenically tipped probe to remove blockage tissue or other undesirable tissue.

A syringe can be connected at the proximal end of each lumen for the delivery of saline liquid to the appropriate location. Each syringe is conventional and includes a piston and an on/off locking valve at its end to retain the liquid in the particular lumen once it has been filled.

In one embodiment, two syringes can be utilized each having a three position valve to connect one syringe to either the lumen feeding the first balloon or the lumen feeding the first liquid orifice, and the other syringe to either the lumen feeding the second balloon or the lumen feeding the second liquid orifice.

In the preferred embodiment, the distance is adjustable between each of the expandable balloons to accommodate the distance of various sized women or various distances between the cervix and the fallopian tube opening, such as to custom fit the more distal balloon within a fallopian tube while the proximal balloon is positioned in the cervical opening. Upon inflation, the cervix opening is blocked with the first balloon to prevent fluid leakage outside the uterus. When the fallopian tube balloon is inflated, saline fluid can be injected into the fallopian tube that is being examined.

In an alternative embodiment, the distance is fixed between the cervix opening balloon and the fallopian tube balloon to fit an average woman's body or for a typical distance between the cervical opening and the fallopian tube.

The catheter device can include a flexible, precurved distal end section having memory that, upon insertion of the distal end, is directed by longitudinal insertion predisposed toward either one fallopian tube opening or the other, because the fallopian tube openings are offset relative to the cervix and uterus. The curved end directs the entire catheter distal end in a preferred direction toward the selected fallopian tube opening, reducing the amount of manipulation required by the surgeon to position the balloon in the fallopian tube opening.

In the preferred embodiment, a three position valve can be provided to connect a first syringe to either a lumen leading to the first balloon or a lumen leading to the first liquid orifice. The third valve position is an "off" position effectively sealing off the lumens and the syringe. When filled with fluid from the first syringe, the first balloon seals the entrance to the uterus permitting fluid flowing from the first syringe to the first liquid orifice to fill the uterus.

A second three position valve can be provided to connected a second syringe to either a lumen leading to the second balloon or a lumen leading to the second liquid orifice. The third valve position being an "off" position effectively sealing off the lumens and the second syringe.

The preferred embodiment of the catheter includes a first and second lumen set side by side in the catheter tube. The first lumen supplies fluid to the first balloon and contains a conduit having a third lumen to supply fluid to the first liquid orifice. The second lumen slidably receives a conduit having a fourth lumen to supply fluid to the second balloon and contains a conduit having a fifth lumen to supply fluid to the second liquid orifice.

The conduit within the second lumen and containing the lumens leading to the second balloon and second liquid orifice slides in relation to the lumens leading to the first balloon and first liquid orifice. This allows for adjustability in the distance between the second balloon and second liquid orifice for the fallopian tubes, and the first balloon and first liquid orifice for the uterus.

The catheter may also include, at the most distal end, an echogenic probe tip and wire that can extend back through the second three position valve for manual manipulation of the probe tip. The conduit within the second lumen may contain a second conduit having a sixth lumen to slidably receive the probe wire. The wire at the proximal end can include a handle grip and may have a plastic body portion extending at least partially between the proximal end and the distal end. At the distal end, the probe tip can be covered with a plastic portion to protect tissue from damage upon insertion, but that may perform physiological operations, such as catheterization.

To use the present invention, the physician or surgeon would manipulate the catheter and its distal end toward the uterus. The catheter is preferably rigid but flexible to permit manipulation and positioning by the physician. When the first balloon is positioned within the cervical opening to the uterus, the first three position valve is turned from the first "off" position to a second position to inflate the first balloon. The first syringe can then inflate the balloon causing a seal around the cervical opening into the uterus. The uterus can then be filled with liquid dispensed by turning the first three position valve to a third position and injecting fluid from the first syringe to the first liquid orifice adjacent the first balloon. The first three position valve can then be turned back to the first (off) position.

Next the slidable conduit within the second lumen is manually slid, relative to the first balloon's seal in the cervical opening, toward one of the fallopian tubes. The interface between the slidable conduit and the second lumen contains a conventional seal, such as an o-ring seal, so fluid within the uterus does not leak out around the conduit and through the second lumen.

The slidable conduit can be somewhat rigid but flexible, and can be provided with a permanent curve such that the distal end automatically tends toward one or the other fallopian tubes during longitudinal insertion. The direction of the curve in the conduit can be controlled by manual rotation during insertion thus directing the distal end toward one or the other desired fallopian tubes.

Once the second balloon is in position within, or near, the ostial opening of the fallopian tube, the second three position valve is turned from the first "off" position to the second position and the second balloon is inflated from the second syringe. Once the selected fallopian tube balloon has been expanded to form a seal around the inside of the fallopian tube opening, the second three position valve is turned to the third position and fluid is dispensed from the second syringe through the second liquid orifice adjacent the second balloon, filling the fallopian tube with the desired liquid.

If so equipped, the echogenic probe tip can then be inserted into the fallopian tube through the sixth lumen to further enhance the ultrasonic examination, and to catheterize any blockage found therein. The interface between the wire and the sixth lumen can include a seal to prevent fluid within the fallopian tube from leaking back through the sixth lumen.

Using the present invention, important saline liquids or other desirable liquids necessary for more accurate ultrasonic investigation and displays can be quickly and easily sealed and trapped in desired body cavities.

It is an object of this invention to provide an improved catheter for providing necessary liquids in a sealed relationship in a fallopian tube and in a uterus for ultrasonic examinations.

It is another object of this invention to provide an adjustable catheter for diagnostic and therapeutic examination of the fallopian tubes.

But yet another object of this invention, in an alternative embodiment, provides two expandable balloons that could be adjusted in distance to provide the proper spacing between the cervical opening to seal the uterus for fluid introduction, while sealing the fallopian tube for fluid introduction by manipulation from the surgeon.

Still another object of this invention is to provide an adjustable echogenic probe tip for catheterization of tissue within the fallopian tubes.

In accordance with these and other objects which will become apparent hereinafter, the instant invention will now be described with particular reference to the accompanying drawings.

BRIEF DESCRIPTION OF THE DRAWINGS

FIG. 3 is a perspective view of the distal probe end of the device in accordance with the present invention.

FIG. 4 is a view taken along line 4—4 of FIG. 1.

FIG. 5 is a schematic top view of the present invention as disposed in portion at the cervical opening to the uterus.

FIG. 6 is a schematic top view of the present invention as disposed in portion at a fallopian tube.

DESCRIPTION OF THE PREFERRED EMBODIMENTS

Figure 1:
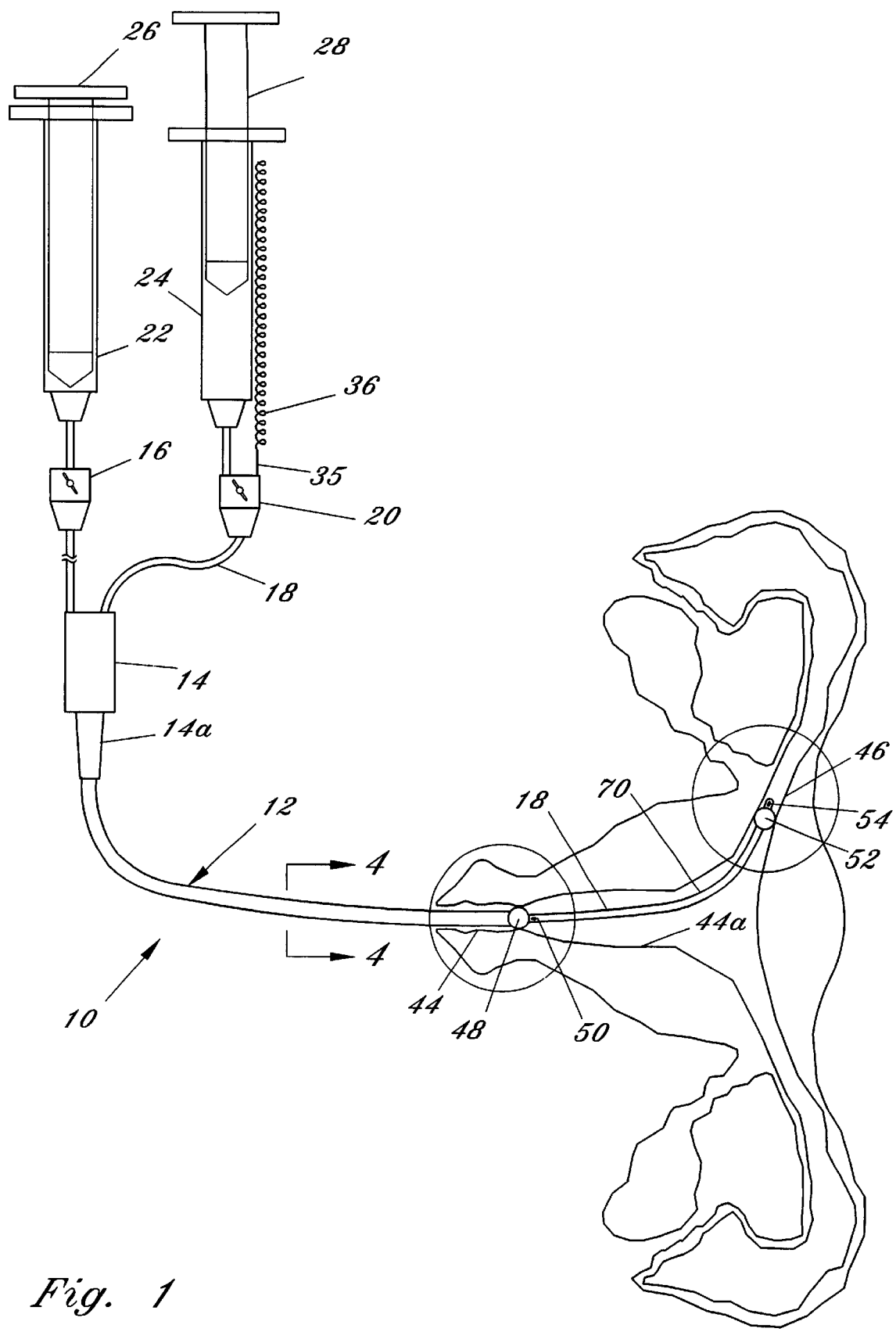
FIG. 1 is a schematic representation of the present invention in a top view, representative of the uterine and fallopian portions of the body, in use.

Referring now to the drawings, and in particular to FIG. 1, the present invention is shown generally at 10, comprised of an extended lumen housing 12 connected at one end to an enlarged handle portion 14 and 14a, and which extends at the proximate end to three position valve 16. Lumen housing 12 slidably receives conduit 18 which extends at the proximate end to three position valve 20.

In the preferred embodiment, the device utilizes two syringes 22, and 24. Syringe 22 is connected to three position valve 16 and syringe 24 is connected to three position valve 20. Three position valves 16 and 20 are manually turned on and off.

Syringes 22 and 24, through the use of plungers 26 and 28, provide fluid, such as saline solution, into lumens within lumen housing 12 and conduit 18 to inflate elastic balloons 48 and 52, and to provide fluid through orifices 50 and 54, as fully described herein below.

The overall purpose of the invention is to fill the uterus 44a by expelling saline fluid from an orifice 50, while expanding balloon 48 to seal off the cervical opening 44, so that fluid is retained in the uterus cavity 44a. Simultaneously, it is desirable to fill the fallopian tube 46 with a saline solution and seal it with an inflated, elastic balloon 52.

The filling of the uterus 44a and the fallopian tube 46 with saline solution is to enhance the use of ultrasonics or sonograms to determine whether or not there is any blockage in the fallopian tube 46.

At the distal end of conduit 18, a probe 35 with a sonogenic tip 72 may be utilized for enhancing ultrasonic examination and performing therapeutic opening or catheterization within the fallopian tube if it is blocked.

Conduit 18 is slidable relative to lumen housing 12, as fully described herein below, to provide adjustable distance between the sealing elastic balloons 48 and 52 to position balloon 48 within the cervical opening 44 and balloon 52 within fallopian tube 46.

In an alternate embodiment, the distance between the sealing, elastic balloons 48 and 52 is predetermined to be the distance that would accommodate an average woman, so that balloon 52 can seal the fallopian tube opening 46, while at the same time balloon 48 will reside in the cervix opening to seal the uterus chamber. In this manner, a plurality of catheters having various fixed distances between balloons 48 and 52 could be made to accommodate women of various sizes. For example, small, medium, and large size catheters could be made each having a different distance between balloon 48 and balloon 52.

Figure 2:
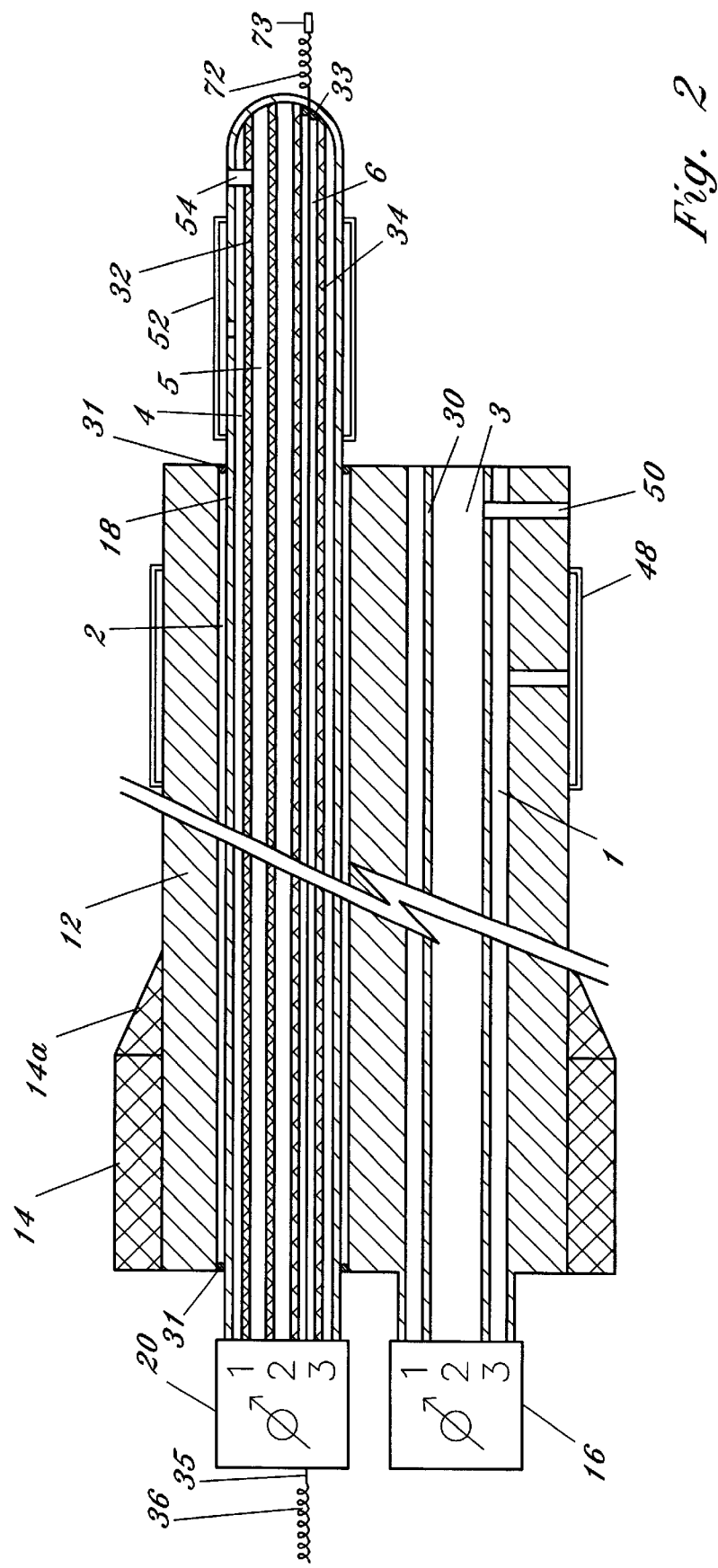
FIG. 2 is a cross-sectional view of the present invention.

Referring to FIG. 2, lumen housing 12 contains lumens 1 and 2. Lumen 1 connects fluid flowing from syringe 22 to balloon 48, through three position valve 16. Lumen 1 also contains conduit 30. Conduit 30 includes lumen 3 which connects fluid flowing from syringe 22 to liquid orifice 50, through three position valve 16. Liquid orifice 50 can be alternately positioned in lumen housing 12, such as axially, as long as liquid orifice 50 is distal to balloon 48.

Lumen 2 slidably receives conduit 18. The interface between lumen 2 and conduit 18 includes at least one conventional seal 31 at the proximal end and/or the distal end. Seal(s) 31 prevent fluid from leaking back from the uterus 44a around conduit 18 and through lumen 2.

Conduit 18 contains lumen 4 which connects fluid flowing from syringe 24 to balloon 52, through three position valve 20. Lumen 4 also contains conduit 32 which contains lumen 5 which connects fluid flowing from syringe 24 to liquid orifice 54, through three position valve 20. Liquid orifice 54 can be alternately positioned in conduit 18, such as axially, as long as liquid orifice 54 is distal to balloon 52.

Lumen 4 can also contain conduit 34 which includes lumen 6. Lumen 6 contains probe 35 which can have a handle portion 36 at the proximal end and a sonogenic tip 72 at the distal end. A sonogenic or echogenic tip is made of known material that enhances the echo received from ultrasonic testing. Sonogenic tip 72 can include a protective end portion or cap 73 which prevents tissue damage during insertion but can still be used to catheterize blockages found, as described herein below. Probe 35, between handle 36 and sonogenic tip 72, can be made of metal such as a wire, or can be plastic, or can include a portion that is plastic and a portion that is metal. Protective end cap 73 can be made of plastic or similar material.

The interface between lumen 6 and probe 35 can include a seal 33 at the distal end, and/or proximate end (not shown) to prevent liquid from leaking back into lumen 6 from the fallopian tube 46.

Each of the lumens 1 through 5 provide separate and independent passages for the transfer and delivery of the saline liquid to inflate the elastic balloons 48 and 52 and deliver fluid to liquid orifices 50 and 54.

The lumen housing 12, and the conduit utilized in the invention, may be made of suitable plastics as known in the art, such as polypropylenes, polyesters, polyvinyl chloride, or other suitable conduit material for the transport of saline liquids. The device may be extruded or formed together as a series of tubes.

The balloons 48 and 52 are essentially thin sheets of latex that are adhered in conventional manner, such as glued, to the corresponding supply tubes in such a way as to inflate circumferentially through the injection of liquid through lumens 1 and 4, causing the elastic latex balloon to inflate outwardly circumferentially, forming a seal across the fallopian and cervical openings. Valves 16 and 20 can be turned on and off so that once fluid is injected, inflating the balloon, the valves 16 and 20 are shut off, holding the balloon in a filled or expanded position.

FIG. 3 shows the distal end of conduit 18 having aperture 54 through which the saline fluid is injected and delivered to the fallopian tube 46. Balloon 52 is shown in a collapsed position, but is a latex band that can be expanded by providing liquid through lumen 4. Probe 35, sonogenic tip 72, and protective cap 73 are illustrated extending through seal 33.

FIG. 4 is a cross-sectional view of the preferred embodiment of lumen housing 12 illustrating the relationship between lumen 1–6, conduit 18, 30, 32, and 34, and probe 35.

Referring to FIG. 5, aperture 50, which is formed in lumen housing 12, allows fluid to be dispensed into the uterus after balloon 48 has been expanded by manually setting three position valve 16 to the appropriate position for inflation, and depressing plunger 26 of syringe 22 (FIGS. 1 and 2). Conduit 18 can then be manually inserted through the uterus 44a toward the fallopian tube 46.

Referring to FIG. 6, a schematic representation of fallopian tube 46 is shown with an inflated balloon 52 sealing the entrance to the fallopian tube 46, allowing a liquid to be dispensed through aperture 54, which would fill the fallopian tube. Once conduit 18 is inserted into the fallopian tube area, the surgeon manually inflates balloon 52 by setting the three position valve 20 to the appropriate position for inflation, and depressing plunger 28 on syringe 24 (FIGS. 1 and 2) to seal the fallopian tube 46.

Referring back to FIG. 1, the overall method used in the present invention is to insert the distal end of the catheter 10 into the cervix opening 44 of the uterus 44a. At this time, the distal end of conduit 18 will be essentially at the distal end of catheter 10. When balloon 48 is in position in the cervical opening 44, balloon 48 is manually inflated by setting three position valve 16 to the appropriate position for inflation, and depressing plunger 26 of syringe 22. The inflation position of three position valve 16 connects lumen 1 between syringe 22 and balloon 48 and seals off lumen 3.

Once balloon 48 is inflated sealing the opening to the uterus 44a, three position valve 16 is manually set to the fill position, and plunger 26 is depressed in syringe 22 to inject saline fluid through orifice 50 filling uterus 44a. The fill position of three position valve 16 connects lumen 3 between syringe 22 and liquid orifice 50, and seals off lumen 1. Three position valve 16 can then be manually turned to the off position sealing lumens 1 and 3.

Next, conduit 18 is manually inserted through lumen 2 in lumen housing 12, and manipulated toward the fallopian tube of interest. Conduit 18 can include a permanent curve 70, to align the distal end of conduit 18 with one or the other fallopian tubes by rotation of the device by the operating surgeon.

Since the distance between balloon 48 and balloon 52 is adjustable, with balloon 48 in the cervical opening, balloon 52 can be properly positioned within the fallopian tube 46 to permit sealing of the fallopian tube when balloon 52 is inflated. Once the positioning has been accomplished, fluid is then introduced to inflate balloon 52 and seal it tightly against the walls of the fallopian tube 46 by manual setting of three position valve 20 to the inflation position and depressing plunger 28 of syringe 24. The inflation position of three position valve 20 connects lumen 4 between syringe 24 and balloon 52, and seals off lumen 5.

Once balloon 52 is inflated sealing fallopian tube 46, three position valve 20 is manually set to the fill position, and plunger 28 is depressed in syringe 24 to inject saline fluid through orifice 54, filling fallopian tube 46. The fill position of three position valve 20 connects lumen 5 between syringe 24 and liquid orifice 54, and seals off lumen 4. Three position valve 20 can then be manually turned to the off position sealing lumens 4 and 5.

At this point in time, both the fallopian tube cavity and the uterine cavity are filled with saline solution to allow proper ultrasonic examination in both areas.

The catheter 10 may also include probe 35 delivered through lumen 6 in conduit 34 which can catheterize detected blockages found beyond the distal end of conduit 18 by insertion of probe 35. Echogenic tip 72 of probe 35 can be utilized to enhance ultrasonic analysis. Tip 72 can have a protective end cap 73, which may be plastic, to prevent unwanted damage to surrounding tissue during insertion of conduit 18 and/or probe 35, but that can still catheterize blockages.

Lumen housing 12 can include seal 31, which can be an o-ring, shaft seal, or other seal to prevent fluid within uterus 44a from leaking back into or entering lumen housing 12 at the slidable interface with conduit 18. Likewise, conduit 34 can include seal 33, which can be similar to seal 31, to keep fluid that is within fallopian tube 46 from entering conduit 34 at the slidable interface with probe 35.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. An apparatus for filling a fallopian tube and sealing the opening to the fallopian tube to be examined with a desirable saline solution for ultrasonic examination, and for simultaneously filling the uterus with a saline solution and sealing the cervix for ultrasonic examination, comprising:

a first conduit having a proximal end and a distal end and a first liquid orifice at said distal end, and having a first lumen and a second lumen;

a first inflatable elastic member sized in diameter to seal a cervical opening when inflated disposed at the distal end of said first conduit and in fluid communication with said first lumen and sealed to said first conduit so that liquid under pressure injected into said first lumen would cause said elastic member to inflate radially, said elastic member disposed adjacent the distal end of said first lumen;

a third lumen having a proximal end and a distal end and in fluid communication with a first liquid orifice in the distal end of said first conduit;

a second conduit having a proximal end and a distal end and a liquid orifice at its distal end, and having a fourth lumen and a fifth lumen, each having proximal and distal ends, said second conduit disposed within said second lumen;

a second elastic member sized to seal a fallopian tube opening when inflated disposed at the distal end of said second conduit and in fluid communication with said fourth lumen and sealed to said second conduit so that liquid under pressure injected into said fourth lumen would cause said second elastic member to inflate radially, said second elastic member disposed adjacent the distal end of said fourth lumen;

said fifth lumen in fluid communication with a liquid orifice in the distal end of said second conduit;

first dispensing means connected to the proximal ends of said first lumen and said third lumen for selectively dispensing a fluid within said first lumen and said third lumen; and second dispensing means connected to the proximal ends of said fourth lumen and said fifth lumen for selectively dispensing liquid within said fourth and said fifth lumens;

wherein said first dispensing means can dispense a saline solution for inflation of said first elastic member for sealing the cervical opening and for delivery to the uterine cavity through said first liquid orifice, and said second dispensing means can dispense a saline solution for inflation of said second elastic member and for delivery to the fallopian tube through said liquid orifice in said second conduit.

2. A device as in claim 1, including:

means for adjusting the distance between said first elastic member and said second elastic member sized to accommodate women of different sizes between the cervical opening and the uterus and the fallopian opening to insure that the first elastic member fits snugly in the cervical opening while the second elastic member is disposed in the proper position in the fallopian tube to insure that the uterus and fallopian tube are sealed for filling with liquid from said first and said second liquid orifices, respectively.

3. A device as in claim 1, wherein said second conduit includes means for insertion of a probe within the fallopian tube through a sixth lumen, said probe having an echogenic distal end and means for catheterization of tissue within the fallopian tube.

4. An improved catheter system for filling a fallopian tube and sealing the opening to a fallopian tube to be examined ultrasonically including filling with a desirable saline solution for ultrasonic examination, and for filling the uterus with a saline solution for ultrasonic examination and for simultaneously sealing the cervical opening to the uterus while at the same time, sealing the opening to the fallopian tube so that during ultrasonic examination, the fallopian tube and the uterus can be filled with a saline solution for ultrasonic examination comprising:

first liquid dispensing syringe;

second liquid dispensing syringe;

first conduit in fluid communication with said first syringe, said first conduit having a first and second lumen, said first conduit having a proximal end and a distal end;

first expandable elastic member, said first expandable elastic member disposed at the distal end of said first conduit and in fluid communication with said first lumen and sealed to said first conduit such that liquid under pressure disposed into said first lumen from said first syringe causes said elastic member to inflate radially, said elastic, inflatable member being sized radially to seal a cervical opening in the inflated position;

a third lumen, said first conduit having a fluid orifice at its distal end, said third lumen in fluid communication with said first conduit orifice;

second conduit having a fourth and fifth lumen, said second conduit disposed within said second lumen, and said second conduit having a proximal end and a distal end;

second elastic member expandable radially and sized to seal a fallopian tube opening when inflated radially disposed at the distal end of said second conduit and in fluid communication with said fourth lumen and sealed to said second conduit so that liquid under pressure injected into said fourth lumen radially enlarges and inflates said second elastic member, said second elastic member disposed adjacent to distal end of said fourth lumen;

said second conduit having a liquid orifice in the distal end of said second conduit, and said fifth lumen in fluid communication with said second conduit liquid orifice;

said first syringe connected to the proximal ends of said first lumen and said third lumen for selectively dispensing a fluid within said first lumen and said third lumen; and said second syringe connected to the proximal ends of said fourth lumen and said fifth lumen for selectively dispensing liquid within said fourth and said fifth lumen;

wherein said first syringe can dispense a saline solution for inflation of said first elastic member for sealing a cervical opening and for delivery to the uterine cavity through said first liquid orifice, and said second syringe can dispense a saline a solution for inflation of said second elastic member and for delivery to a fallopian tube opening through said second liquid orifice for enhancing ultrasonic examination.

5. A device as in claim 4, including means for adjusting the distance between said first elastic member and said second elastic member, said adjustable distance being sized to accommodate women having physiological different distances between cervical openings and the uterus and fallopian tube openings to ensure that the first elastic member fits snugly in a cervical opening while the second elastic member is disposed in the proper position in a fallopian tube opening to ensure that the uterus and the fallopian tube are sealed for filling with liquid from said first and second orifices respectively to enhance ultrasonic examination.

* * * * *